(12) United States Patent
Loy et al.

(10) Patent No.: US 6,284,908 B1
(45) Date of Patent: Sep. 4, 2001

(54) METHOD FOR MAKING POLYSILSESQUIOXANES AND ORGANOHYDRIDOSILANES

(75) Inventors: Douglas A. Loy; Kamyar Rahimian, both of Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/669,101

(22) Filed: Sep. 25, 2000

(51) Int. Cl.$^7$ ........................................... C07F 12/08
(52) U.S. Cl. ................... 556/467; 528/14; 528/21
(58) Field of Search ............... 556/467; 528/14, 528/21

(56) References Cited

U.S. PATENT DOCUMENTS

| | | | |
|---|---|---|---|
| 4,417,067 | * 11/1983 | Kotzsch et al. | 556/467 |
| 4,528,390 | 7/1985 | Kimura | 528/25 |
| 5,504,235 | * 4/1996 | Hirose et al. | 556/467 |
| 5,892,087 | * 4/1999 | Yung et al. | 556/467 |
| 6,043,330 | 3/2000 | Hacker et al. | 528/10 |

OTHER PUBLICATIONS

Laine, R., Rahn, J. Youngdahl, K., Babonneau, F., Hoppe, M., Zhang, Z., and Harrod, J., "Synthesis and high-temperature chemistry of methylsilsesquioxane polymers produced by titanium–catalyzed redistribution of methylhydridooligo– and –polysiloxanes," Chem. Mater., 1990, 2, 464–472.

Xin, S., Aitken, C., Harrod, J., Mu, Y., and Samuel, E., "Redistribution reactions of alkoxy– and siloxysilanes, catalyzed by dimethyltitanocene," Can. J. Chem., 1990, 68, 471–476.

Rahimian, K., Assink, R. and Loy, D., "Polymethylsilsesquioxanes through base–catalyzed redistribution of oligomethylhydridosiloxanes," Polymer Preprints, American Chemical Society, 2000, 41(1), 512–513.

Rahimian, K., Assink, R., Lang, D., and Loy, D., "Polysilsesquioxanes through base–catalyzed redistribution of oligohydridosiloxanes," Polymer Preprints, American Chemical Society, 2000, 41 (2), 1277–1278.

* cited by examiner

Primary Examiner—Paul F. Shaver
(74) Attorney, Agent, or Firm—Elmer A. Klavetter

(57) ABSTRACT

A method for disproportionation of an oligohydridosiloxane to produce a polysilsesquioxane compound and an organohydridosilane compound when contacted with a basic catalyst. The basic catalyst can be a tetraalkylammonium hydroxide, an alkali metal hydroxide, and an alkali earth hydroxide. These basic catalysts are generally dissolved in an organic solvent for delivery. The hydroxide catalysts are attractive because many readily decompose by heating above 150° C., thus being easily removed from the final materials. The oligohydridosiloxane is contacted with the basic catalyst under conditions effective to catalytically convert the oligohydridosiloxane into a polysilsesquioxane compound and an organohydridosilane compound. The reaction can occur in either an inert or oxidative atmosphere and can occur without heating, at room temperature. Both polysilsesquioxane foams and gels of the formula $(RSiO_{1.5})_n$ can be produced.

16 Claims, No Drawings

METHOD FOR MAKING POLYSILSESQUIOXANES AND ORGANOHYDRIDOSILANES

This invention was made with Government support under Contract No. DE-AC04-94AL85000 awarded by the United States Department of Energy. The Government has certain rights in the invention.

BACKGROUND OF THE INVENTION

The present application is generally directed to a method of making polysilsesquioxane and organohydridosilane compounds and, more particularly, to a base-catalyzed, disproportionation method of making polysilsesquioxane and organohydridosilane compounds.

Organopolysilsesquioxanes have applications as material for low-K dielectrics, ceramic precursors and photoresists. Organohydridosilane compounds have applications in the electronic and semiconductor fields to coat silicon chips and other components, serving as protective coatings and inter-level dielectric layers.

Polysilsesquioxane compounds can be produced by hydrolytic condensation of a silane in an aqueous solution of ammonia or an amine. However, organohydridosilanes are not produced (Kimura, U.S. Pat. No. 4,528,390).

Polysilsesquioxanes can also be made using a sol-gel synthesis method involving the hydrolysis of some organotricholorosilanes or organotrialkoxysilanes in the presence of acid or base catalysts and organic solvents. However, under sol-gel conditions most organotrialkoxysilanes do not afford silsesquioxane gels. This limits the range of organic functionalities that can be introduced into these hybrid organic-inorganic materials. This polymerization process also requires solvent and stoichiometric water and produces alcohol and water condensation by-products.

In an alternative route to polysilisesquioxanes, catalytic disproportionation, by titanium complexes, of linear or cyclic oligomers of methylhydridosiloxanes have produced polymethylsilsesquioxanes (R. Laine, J. Rahn, K. Youngdahl, F. Babonneau, M. Hoppe, Z. Zhang, and J. Harrod, Chem. Mater., 1990, 2, 464–472). This process requires inert conditions because of the moisture and air sensitivity of the titanium catalyst. Redistristribution reactions of alkoxy-and siloxysilanes have also been demonstrated using dimethyltitanocene catalysts (S. Xin, C. Aitken, J. Harrod, Y. Mu, and E. Samuel, Can. J. Chem, 1990, 68, 471–476).

Hydridosiloxanes and organohydridosiloxanes can be produced by catalyzing the hydrolysis and condensation of a silane monomer, where the silane monomer is contacted with a phase transfer catalyst in the presence of a reaction mixture comprising a nonpolar or polar solvent (Hacker et al., U.S. Pat. No. 6,043,330).

DETAILED DESCRIPTION OF THE INVENTION

In the method of the present invention, disproportionation of an oligohydridosiloxane produces a polysilsesquioxane compound and an organohydridosilane compound when contacted with a basic catalyst. Disproportionation is a chemical reaction in which one compound acts as both an oxidizing and a reducing agent, thus yielding two products, namely a more reduced compound and a more oxidized compound. The basic catalyst can be a tetraalkylammonium hydroxide, such as tetramethylammonium hydroxide, tetraethylammonium hydroxide, tetrapropylammonium hydroxide and tetrabutylammonium, as well as an alkali metal hydroxide, such as sodium hydroxide and potassium hydroxide or an alkali earth hydroxide, such as magnesium hydroxide, calcium hydroxide, strontium hydroxide, and barium hydroxide. These basic catalysts are generally dissolved in a solvent for delivery. The solvent can be any organic solvent that dissolves the basic catalysts. The tetraalkylammonium hydroxides are attractive because they readily decompose by heating above 150° C., thus being easily removed from the final materials. The oligohydridosiloxane is contacted with the basic catalyst under conditions effective to catalytically convert the oligohydridosiloxane into a polysilsesquioxane compound and an organohydridosilane compound. The reaction can occur in either an inert or oxidative atmosphere and can occur without heating, at room temperature. Both polysilsesquioxane foams and gels of the formula $(RSiO_{1.5})_n$ can be produced, which otherwise cannot be obtained easily, if at all, through traditional sol-gel means. In this formula, R can be any functionalized or non-functionalized alkyl or aromatic group where n indicates that a polymer is produced (Rahimian, K.; Lang, D. P.; Loy, D. A., Polym. Prepr., Am. Chem. Soc., Div. Polym. Chem., (2000), 41(2), 1277–1278; Rahimian, K.; Assink, R. A.; Loy, D. A, Polym. Prepr., Am. Chem. Soc., Div. Polym. Chem., 2000, 41(1), 512–513; incorporated by reference herein).

The oligohydridosiloxane that undergoes the disproportionation reaction is not limited to any particular functional substitution but can be any oligohydridosiloxane compound of the general formula $(RHSiO)_n$ or mixture of oligohydridosiloxane compounds, where R is an alkyl group, such as a methyl, ethyl, propyl or butyl group, or an aromatic group, such as a benzyl or phenyl group and n is equal to or greater than one. Co-oligomer compounds, such as methylhydrido compounds with dimethyl, octyl-methyl and phenyl-methyl siloxanes, such as a methylhydridosiloxane-dimethylsiloxane copolymer, a methylhydridosiloxane-octylmethylsiloxane copolymer, and a methylhydridosiloxane-phenylmethylsiloxane copolymer can also be used. The co-oligomer compounds or co-polymers have the general formula $(RSiO_{1.5})_n (R'R''SiO)_m$ where m is greater than or equal to one and R' and R" are alkyl or aryl groups. Aryl or alkyl hydridosilanes of the general formula $RSiH_3$ and polysilsesquioxanes of the formula $(RSiO_{1.5})_n$ are produced.

In traditional means to produce polysilsesquioxanes, alkoxysilanes or chlorosilanes are reacted with a catalyst (base or acid) in the presence of water, which is needed for the hydrolysis of the alkoxy groups and the reaction of the chloride, in a solvent required to solubilize the reactants. In the method of the present invention, hydrolysis does not occur and no condensation products are generated but two useful products, the polysilsesquioxanes and the organohydridosilanes, are produced.

In one embodiment, the oligohydridosiloxane is contacted with the catalyst in a polar solvent, such as tetrahydrofuran (THF) or methanol or a nonpolar solvent, such as benzene. The solvent is utilized to enhance the degree of completion and provide that the catalyst is in a liquid phase that can be admixed with the oligohydridosiloxane. However, the reaction can also be performed in neat conditions where conversions of up to 75% can be reached depending on the amount of catalyst used.

In a typical reaction, the oligohydridosiloxane, such as [RHSiO]$_n$ (R=Me, Et, Ph) and [MeHSiO]$_n$[Me$_2$SiO]$_n$, was weighed out in a flask and catalytic amounts of the catalyst, such as tetrabutylammonium hydroxide (TBAH) (0.1N solution in MeOH/toluene) were added. The reaction, performed both under argon atmosphere and repeated in air, is exothermic and immediate generation of RSiH$_3$ was observed; for R=Me, Et, the silane is gaseous and is released from the reaction. For R=Me, Et, as more RSiH$_3$ is generated, the product gets more viscous, and within one minute the reaction solidifies. For R=Ph, PhSiH$_3$ is not isolated from the reaction and becomes part of the final product. At high catalyst concentrations (1.00 mol %), the reaction is very exothermic, violent and can erupt out of the reaction vessel. Reactions were also performed in THF. The oligohydridosiloxane was placed in a flask and diluted with THF. TBAH was slowly added to the reaction, the reaction was stirred overnight (for approximately 12 hours) and the volatiles were removed in vacuo (0.01 Torr). In these reactions, both a polysilsesquioxane compound and an organohydridosilane compound were produced. Based on spectroscopic data, all of the SiH functionality was converted to RSiH$_3$.

In one embodiment, oligomethylhydridosiloxane was contacted with TBAH as shown below:

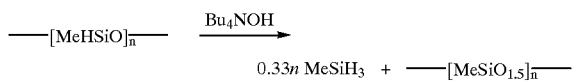

The reaction is exothermic and very rapid. As the amount of TBAH catalyst is increased, so does the exothermicity of the reaction and the rate of the reaction. The reaction solidifies within one minute of TBAH addition. For R=Me, Et, as RSiH$_3$ gas is produced during the reaction (confirmed by $^1$H NMR spectroscopy of the gas evolved), the resulting material foams under neat conditions and can discharge out of the reaction vessel. Under neat conditions, not all of the SiH groups can be converted to MeSiH$_3$, as the reaction is so rapid that it solidifies before the redistribution reaction has a chance to reach completion. This was demonstrated by solid state NMR spectroscopy, which indicated conversion to silsesquioxane silicons of approximately 75%.

The reaction can be driven to completion when performed in a solvent, such as THF, and under dilute conditions (0.012M solution in THF, 2.0 mol % TBAH based on repeating units (r.u.)-(RSiHO) of the starting oligomer) and the mixture allowed to react longer periods (e.g., overnight). Still, at higher concentrations (0.30 M in THF based on r.u.), upon addition of the TBAH catalyst (1.0 mol % TBAH based on r.u.) the solution gels and the reaction does not reach completion.

In another embodiment, a PMHS/PDMS copolymer (PDMS=dimethylsiloxane) was contacted with the catalyst TBAH. As the amount of TBAH catalyst was increased, more MeSiH$_3$ was produced; also, all of the SiH portion of the copolymer was converted when the reaction was performed in solvent and allowed to reach completion, or when sufficient catalyst was added. The linearity content in the final product can be varied by simply varying the amount of the PDMS portion of the starting oligomer. This methodology provides easy access to silsesquioxane polymers that can not be easily accessed by other means.

For the following copolymer systems, the reaction reaches completion and does not foam, only becomes more viscous: PMHS/PDMS, 15:85; PMHS/PoctMeS, 25:75. For all other PMHS/PDMS copolymer systems tested, as well as PMHS/PPhMeS, the reactions foamed and solidified before all of the SiH functionality was converted. For these reactions, the formation of the foam was within five minutes of addition of the TBAH catalyst. The amount of catalyst added in all reactions was approximately 0.5 mol %, based on MeHSiO repeating units.

The invention being thus described, it will be apparent to those skilled in the art that the same may be varied in many ways. Such variations are not to be regarded as a departure from the spirit and scope of the invention, and all such modifications are intended to be included within the scope of the following claims.

We claim:

1. A method for making a polysilsesquioxane compound and an organohydridosilane compound, comprising:

contacting an oligohydridosiloxane of the formula (RHSiO)$_n$, where R is an alkyl or aromatic group, with a basic catalyst, said basic catalyst selected from the group consisting of a tetraalkylammonium hydroxide, an alkali metal hydroxide, and an alkaline earth hydroxide, under conditions effective to catalytically convert said oligohydridosiloxane into a polysilsesquioxane compound and an organohydridosilane compound.

2. The method of claim 1 wherein the oligohydridosiloxane is selected from an oligoalkyllhydridosiloxane and an oligoarylhydridosiloxane.

3. The method of claim 2 wherein the oligoalkylhydridosiloxane is selected from oligomethylhydridosiloxane, oligoethylhydridosiloxane, oligopropylhydridosiloxane, and oligobutylhydridosiloxane.

4. The method of claim 2 wherein the olioarylhydridsiloxane is an oligophenylhydridosiloxane.

5. The method of claim 1 wherein the tetraalkylammonium hydroxide is selected from tetramethylammonium hydroxide, tetraethylammonium hydroxide, tetrapropylammonium hydroxide, and tetrabutylammonium hydroxide.

6. The method of claim 1 wherein the method of contacting an oligohydridosiloxane with a basic catalyst occurs in an atmosphere selected from an inert gas and an oxygen-containing air.

7. The method of claim 1 wherein the contacting of the oligohydridosiloxane with a basic catalyst occurs in an organic solvent in which the oligohydridosiloxane is miscible.

8. The method of claim 7 wherein the solvent is selected from an alcohol, tetrahydrofuran and benzene.

9. The method of claim 7 wherein contacting the oligohydridosiloxane with a basic catalyst occurs in a nonaqueous phase.

10. The method of claim 1 wherein contacting an oligohydridosiloxane with a basic catalyst occurs in the presence of a copolymer.

11. The method of claim 10 wherein the copolymer is selected from dimethylsiloxane, octylmethylsiloxane, and phenylmethylsiloxane.

12. The method of claim 1 wherein the polysilsesquioxane compound formed is a gel.

13. The method of claim 1 wherein the polysilsesquioxane compound formed is a foam.

14. A method for making a polysilsesquioxane compound and an organohydridosilane compound, comprising:

contacting oligomethylhydridosiloxane of the formula $(RHSiO)_n$, where Re is selected from a methyl group, an ethyl group or a phenyl group, with tetrabutylammonium hydroxide under conditions effective to catalytically convert said oligomethyihydridosiloxane into the polysilsesquioxane compound $(RSiO_{1.5})_n$ and the organohydridosilane compound $RSiH_3$.

15. The method of claim 14 wherein the tetrabutylammonium hydroxide is dissolved in a polar solvent.

16. The method of claim 15 wherein the tetrabutylammonium hydroxide has a concentration less than 1 mole percent.

\* \* \* \* \*